(12) United States Patent
Baba et al.

(10) Patent No.: US 10,912,912 B2
(45) Date of Patent: Feb. 9, 2021

(54) GAS MEASUREMENT ADAPTER

(71) Applicant: NIHON KOHDEN CORPORATION, Tokyo (JP)

(72) Inventors: Yuya Baba, Tokorozawa (JP); Masayuki Inoue, Tokorozawa (JP); Hidetoshi Dainobu, Tokorozawa (JP); Kenichiro Kabumoto, Tokorozawa (JP); Fumihiko Takatori, Tokorozawa (JP); Takayuki Aoyagi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 16/143,608

(22) Filed: Sep. 27, 2018

(65) Prior Publication Data

US 2019/0105457 A1 Apr. 11, 2019

(30) Foreign Application Priority Data

Oct. 5, 2017 (JP) ................................. 2017-195009

(51) Int. Cl.
*G01N 33/497* (2006.01)
*A61M 16/08* (2006.01)
(Continued)

(52) U.S. Cl.
CPC ............ *A61M 16/085* (2014.02); *A61B 5/083* (2013.01); *A61B 5/097* (2013.01); *A61M 16/08* (2013.01);
(Continued)

(58) Field of Classification Search
CPC ..... A61B 5/097; A61B 5/0836; A61B 5/0833; A61M 16/085; A61M 16/08;
(Continued)

(56) References Cited

U.S. PATENT DOCUMENTS 5,067,492 A * 11/1991 Yelderman ........... A61B 5/0836
128/204.23
6,216,692 B1 4/2001 Todokoro et al.
(Continued)

FOREIGN PATENT DOCUMENTS

JP 2000-074822 A 3/2000

OTHER PUBLICATIONS

Extended European Search Report issued in Patent Application No. EP 18 19 8180 dated Dec. 21, 2018.
(Continued)

*Primary Examiner* — Brandi N Hopkins
(74) *Attorney, Agent, or Firm* — Pearne & Gordon LLP (57) ABSTRACT

A gas measurement adapter includes a flow tube portion configured to allow gas to pass through the flow tube portion, and a window portion configured to allow measurement light for measuring a component of the gas passing through the flow tube portion to pass through the window portion. The window portion is thinner than the flow tube portion and is molded integrally with the flow tube portion. The window portion comprises an effective portion configured to allow the measurement light to pass through the effective portion and an outer peripheral portion provided on an outer periphery of the effective portion. An inner surface of the window portion is configured such that an outer perimeter of the effective portion is contiguously coplanar with the outer peripheral portion.

15 Claims, 5 Drawing Sheets

(51) Int. Cl.
*A61B 5/097* (2006.01)
*A61B 5/083* (2006.01)

(52) U.S. Cl.
CPC ........ *A61B 5/0836* (2013.01); *A61M 16/0808* (2013.01); *A61M 16/0875* (2013.01); *A61M 2230/432* (2013.01); *G01N 33/497* (2013.01)

(58) Field of Classification Search
CPC .............. A61M 16/0808; G01N 21/05; G01N 21/0303; G01N 2021/0321; G01N 21/3504; G01N 21/645; G01N 33/497; G01N 2001/2244; G01N 21/6428; G01N 33/0036; G01N 2021/6432; G01N 2021/0389; G01F 1/40; B29L 2031/753; B29C 45/16
See application file for complete search history.

(56) References Cited

U.S. PATENT DOCUMENTS

| | | | |
|---|---|---|---|
| 6,512,581 B1 | 1/2003 | Yamamori et al. | |
| 2002/0029003 A1* | 3/2002 | Mace .................... | A61B 5/087 600/532 |
| 2009/0320846 A1 | 12/2009 | Tappehorn et al. | |
| 2011/0028858 A1* | 2/2011 | Dainobu ................ | A61B 5/097 600/532 |

OTHER PUBLICATIONS

European Office action issued in European Patent Application No. 18 198 180.4 dated Nov. 13, 2019.

\* cited by examiner

GAS MEASUREMENT ADAPTER

CROSS-REFERENCE TO RELATED APPLICATION

The present application claims priority from Japanese Patent Application No. 2017-195009 filed on Oct. 5, 2017, the entire content of which is incorporated herein by reference.

BACKGROUND

The presently disclosed subject matter relates to a gas measurement adapter used for measuring gas.

An airway adapter having a transparent window is attached to a flow path of a ventilator that artificially ventilates a patient in order to measure a specific component of gas such as respiratory gas. The respiratory gas passing through the airway adapter contains moisture and water droplets resulting from the moisture slide along the inner wall of the airway adapter. When the water droplets pass by the transparent window, the water droplets block infrared rays for the measurement and cause measurement errors. In view of this, a related art airway adapter has a frame that protrudes from an inner peripheral surface of a flow tube to surrounds the transparent window, so that the water droplets passes along the outer side of the frame (see, e.g., JP2000-074822A).

However, the related art airway adapter has a stepped portion between the window and the frame. This stepped portion can cause the water droplets to accumulate in the gravity direction at the stepped portion and reduce the amount of infrared light passing through the transparent window, which may cause measurement errors.

SUMMARY

One or more aspect of the presently disclosed subject matter provides a gas measurement adapter capable of suppressing measurement errors caused by water droplets.

According to an aspect of the presently disclosed subject matter, a gas measurement adapter includes a flow tube portion configured to allow gas to pass through the flow tube portion, and a window portion configured to allow measurement light for measuring a component of the gas passing through the flow tube portion to pass through the window portion. The window portion is thinner than the flow tube portion and is molded integrally with the flow tube portion. The window portion comprises an effective portion configured to allow the measurement light to pass through the effective portion and an outer peripheral portion provided on an outer periphery of the effective portion. An inner surface of the window portion is configured such that an outer perimeter of the effective portion is contiguously coplanar with the outer peripheral portion.

According to another aspect of the presently disclosed subject matter, a gas measurement adapter includes a flow tube portion configured to allow gas to pass through the flow tube portion, and a window portion configured to allow measurement light for measuring a component of the gas passing through the flow tube portion to pass through the window portion. The window portion is thinner than the flow tube portion and is molded integrally with the flow tube portion. An outer perimeter of the window portion on an inner surface of the window portion is contiguously coplanar with a portion of the flow tube portion bordering the outer perimeter of the window portion.

DETAILED DESCRIPTION

Hereinafter, embodiments of the presently disclosed subject matter will be described with reference to the drawings. In the specification and the drawings, the terms "upper", "lower", "left", "right", "front", and "rear" are used for convenience to illustrate positional relationships between elements, and are not intended to limit an orientation in actual use.

Figure 1:
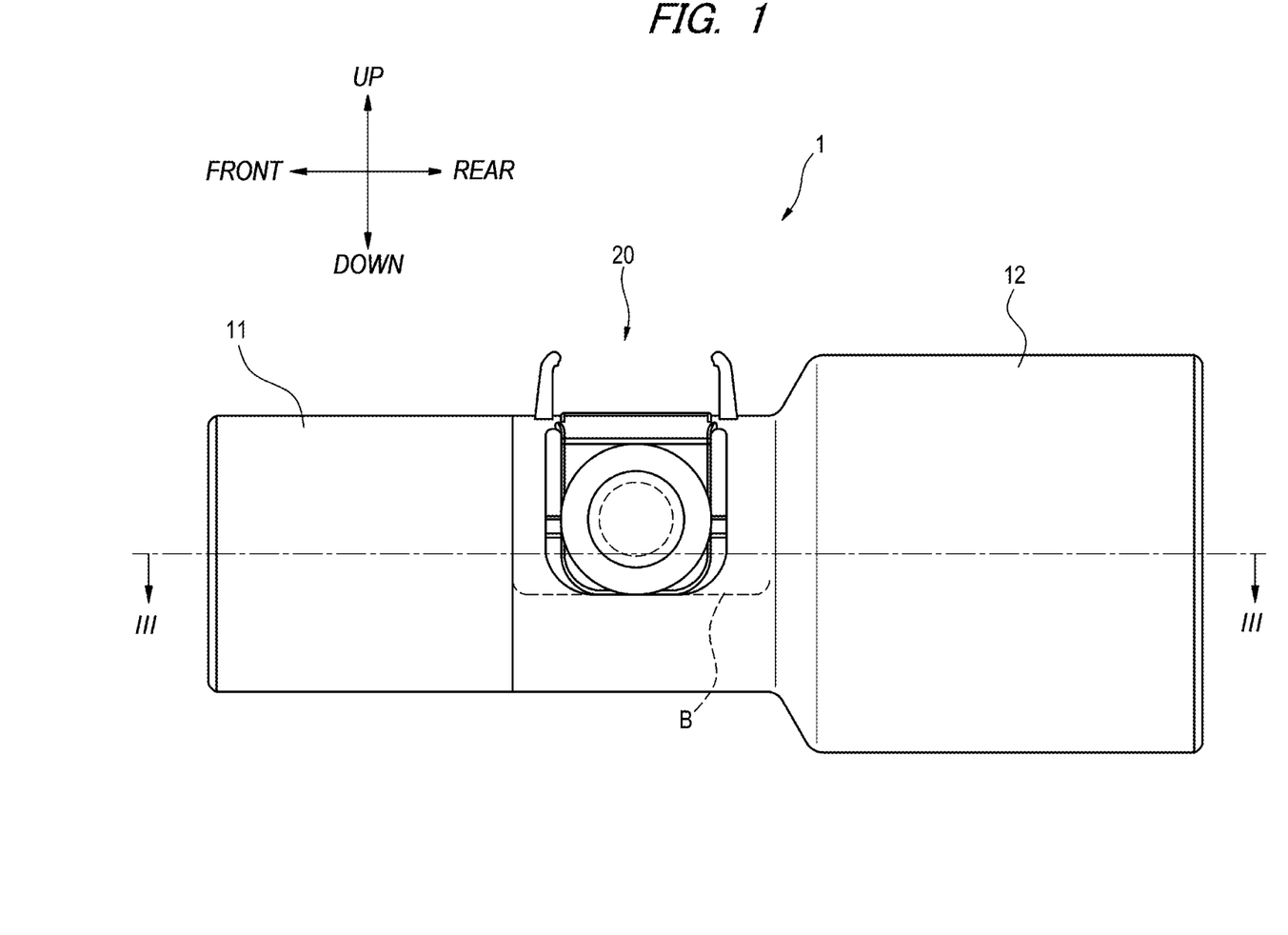
FIG. 1 is a left side view of a gas measurement adapter according to an embodiment of the presently disclosed subject matter.

FIG. 1 is a left side view of a gas measurement adapter 1 according to an embodiment of the presently disclosed subject matter. The gas measurement adapter 1 is configured, for example, to optically measure a concentration of a specific component (e.g., carbon dioxide) contained in respiratory gas of a patient requiring respiratory care (hereinafter referred to as a subject).

As illustrated in FIG. 1, the gas measurement adapter 1 includes a first connection adapter 11 provided at a front end, a second connection adapter 12 provided at a rear end, and a sensor mounting portion 20 provided between the first connection adapter 11 and the second connection adapter 12. The left side surface and the right side surface of the gas measurement adapter 1 have a symmetrical configuration.

The first connection adapter 11 has a cylindrical shape, and is connected to an air supply source and an exhalation discharge port of a ventilator through a connection member such as a Y-tube. The second connection adapter 12 has a cylindrical shape having a larger diameter than the first connection adapter 11, and is connected to a device on the subject side, such as a tracheal tube or a mask.

Figure 2:
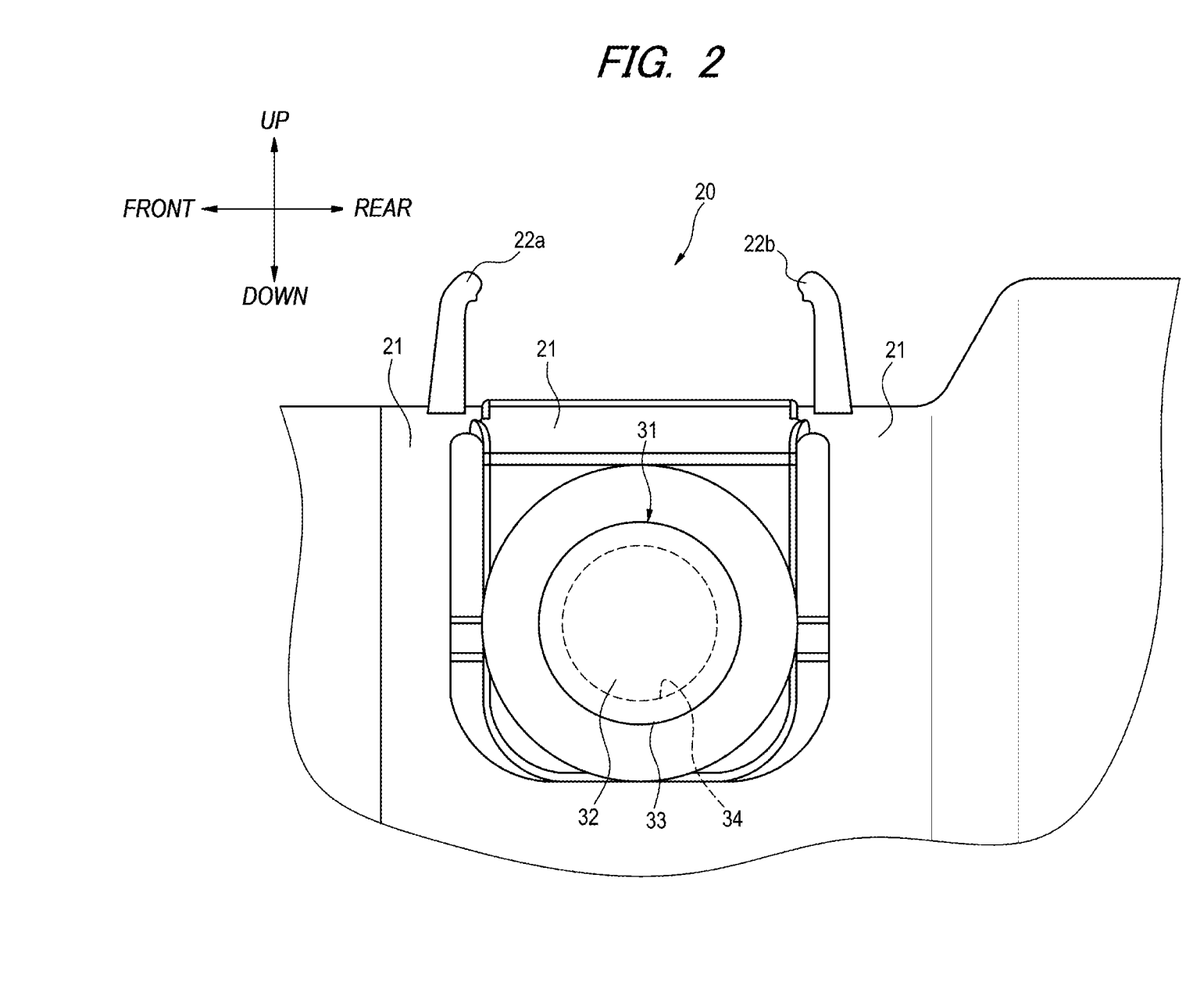
FIG. 2 is an enlarged partial enlarged view of a sensor mounting portion of FIG. 1.

FIG. 2 is an enlarged partial enlarged view of the sensor mounting portion 20 of the gas measurement adapter 1. For example, a respiratory gas concentration sensor (not shown) for optically measuring the concentration of a specific gas contained in the respiratory gas of the subject is attached to the sensor mounting portion 20. As shown in FIG. 2, the sensor mounting portion 20 has a flow tube portion 21 through which the subject's respiratory gas passes, and a window portion 31 provided at the central part of the flow tube portion 21.

The flow tube portion 21 allows the respiratory gas of the subject flowing in from the second connection adapter 12 to pass toward the exhalation discharge port (not shown) connected to the first connection adapter 11. The window portion 31 allows light (e.g., infrared light) to pass through the window portion 31 to measure a component of the respiratory gas passing through the flow tube portion 21. The window portion 31 is provided on each side of the sensor mounting portion 20, i.e., the left side and the right side of the sensor mounting portion 20 in an opposed manner.

When the respiratory gas concentration sensor is attached to the sensor mounting portion 20, the light emitter and the light detector of the respiratory gas concentration sensor are disposed to face the pair of window portions 31 respectively. The respiratory gas concentration sensor attached to the sensor mounting portion 20 is locked by a pair of locking members 22a, 22b provided in an opposed manner at the upper portion of the sensor mounting portion 20, and is positioned in place.

Each window portion 31 has an effective portion 32 configured to allow light for measuring a component of respiratory gas to pass through the window portion 31 and an outer peripheral portion 33 provided at the outer periphery of the effective portion 32. In FIG. 2, the outer perimeter 34 of the effective portion 32 is indicated by a broken line. The light from the respiratory gas concentration sensor passes through the window portions 31 that are arranged in an opposed manner. The effective portion 32 is the area through which the light effective for measuring a component of respiratory gas component (the measurement light) passes through the window portion 32.

The window portion 31 is thinner than the flow tube portion 21, and is molded integrally with the flow tube portion 21. The phrase "molded integrally" means that the window portion 31 and the flow tube portion 21 are molded as a single-piece member. For example, the window portion 31 and the flow tube portion 21 may be molded integrally by resin molding method including injection molding. The window portion 31 and the flow tube portion 21 are preferably made of a material having high fluidity in the mold and having a suitable light absorptivity with respect to the measurement light.

Figure 3:
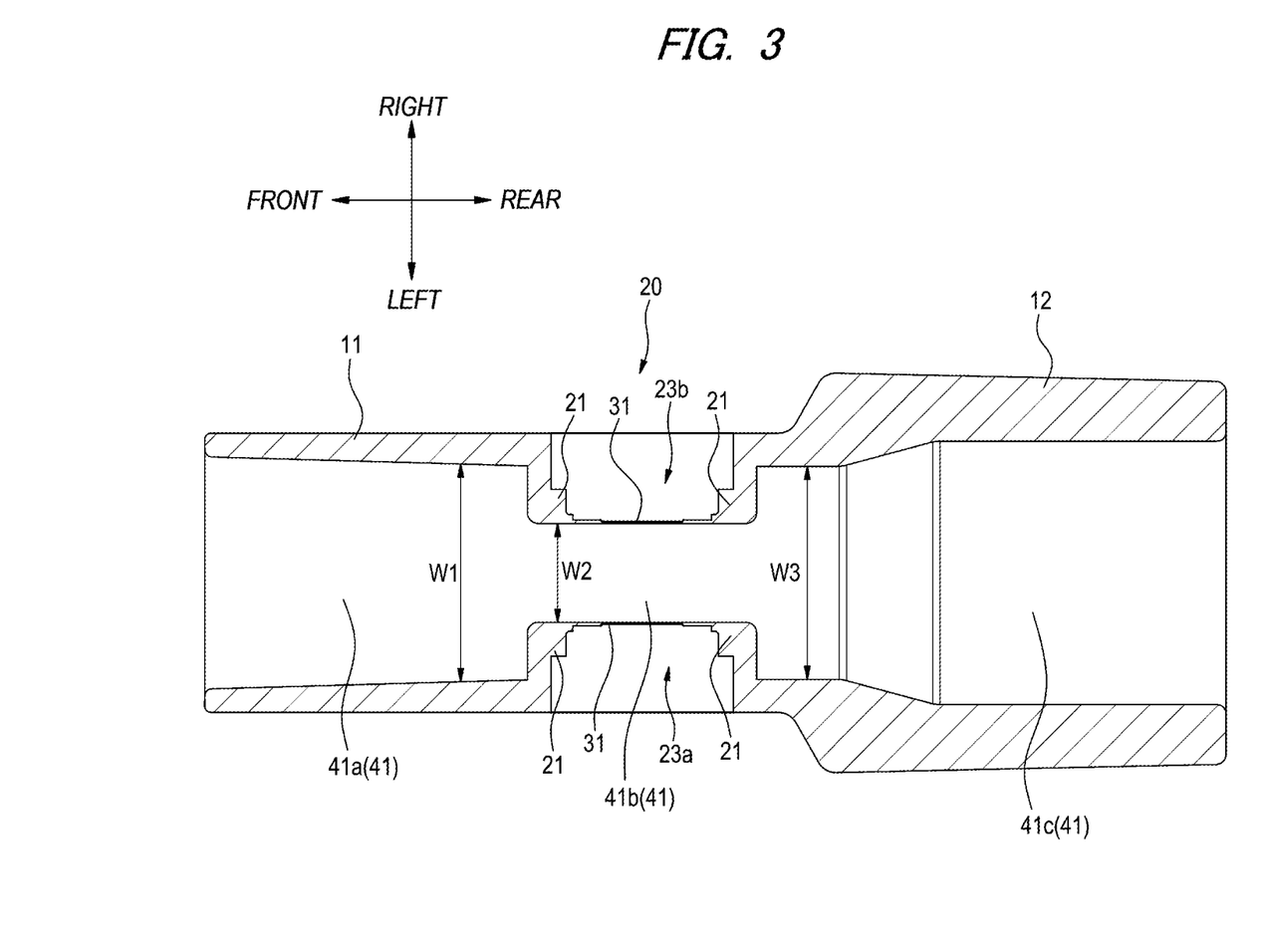
FIG. 3 is a sectional view taken along the line of FIG. 1.

FIG. 3 is a cross-sectional view taken along the line of FIG. 1, illustrating an internal structure of the gas measurement adapter 1. As illustrated in FIG. 3, ventilation passages 41 (41a, 41b, 41c) are provided inside in the gas measurement adapter 1 for the ventilation of the subject's respiratory gas. The ventilation passage 41 is configured as, for example, a single passage through which the ventilation passage 41a in the first connection adapter 11, the ventilation passage 41b in the sensor mounting portion 20, and the ventilation passage 41c in the second connection adapter 12 communicate each other.

The ventilation passage 41a of the first connection adapter 11 and the ventilation passage 41c of the second connection adapter 12 are each formed in a cylindrical shape. The ventilation passage 41b of the sensor mounting portion 20 is formed in a rectangular shape whose width W2 in the left-right direction is narrower than the width in the up-down direction. The width W2 of the ventilation passage 41b in the left-right direction is narrower than the width W1 of the ventilation passage 41a in the left-right direction (the diameter of the ventilation passage 41a) and the width W3 of the ventilation passage 41c in the left-right direction (the diameter of the ventilation passage 41c). As illustrated in FIG. 1, the width of the ventilation passage 41b in the up-down direction is the same as the width of the ventilation passage 41a in the up-down direction (the diameter of the ventilation passage 41a). In the illustrated example, the left-right direction is a light passing direction in which the measurement light passes through the gas measurement adapter 1 via the window portion 31, and the up-down direction is a direction perpendicular to the light passing direction and a gas flow direction in which the respiratory gas flowing in from the second connection adapter 12 passes toward the first connection adapter 11.

The ventilation passage 41b having a narrower width in the left-right direction is provided to extend at least to a position corresponding to the lower end of the window portion 31 in the up-down direction of the sensor mounting portion 20. For example, in the present illustrated embodiment, the ventilation passage 41b is provided to extend to a position of the broken line B shown in FIG. 1. A portion of the ventilation passage 41b below the broken line B (the bottom portion of the ventilation passage 41b) is formed in the same shape as the bottom portion of the ventilation passage 41a of the first connection adapter 11.

Recesses 23a, 23b are formed on the left and right sides of the sensor mounting portion 20. These recesses 23a, 23b are concave portions into which the respiratory gas concentration sensor is fitted, and a window portion 31 is formed in the central part thereof. The recesses 23a, 23b are defined by an outer surfaces of the window portions 31 and outer surfaces of the flow tube portion 21 provided around the window portion 31.

Figure 4:
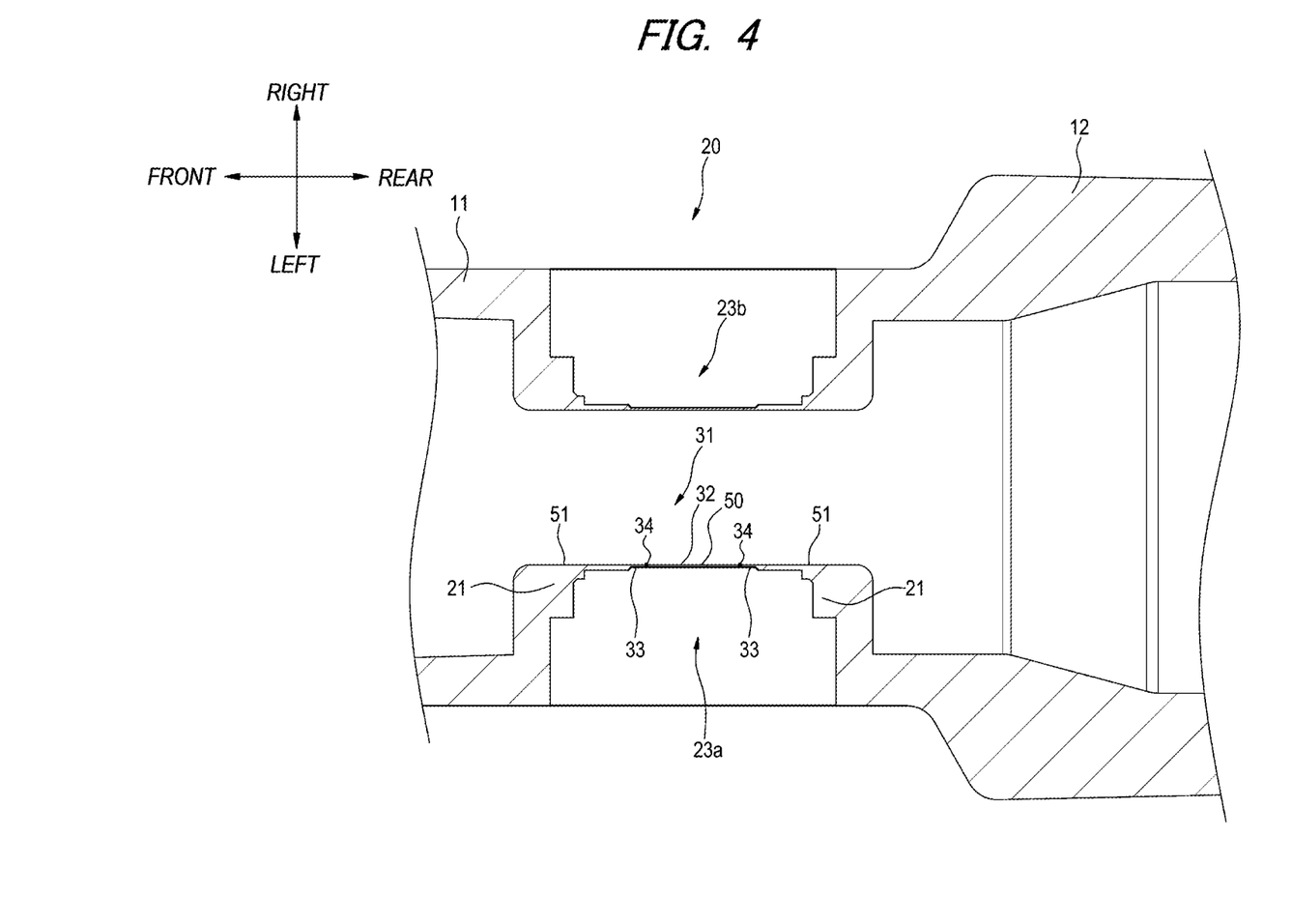
FIG. 4 is an enlarged view of the sensor mounting portion of FIG. 3.

FIG. 4 is an enlarged partial enlarged view of the inside of the sensor mounting portion 20. As shown in FIG. 4, the thickness of the window portion 31 having the effective portion 32 and the outer peripheral portion 33 is formed to have a uniform thickness. The thickness of the flow tube portion 21 depends on a location and varies in accordance with the shape of the concave portions 23a, 23b. The thickness of the window portion 31 is thinner than the thickness of the flow tube portion 21.

The inner surface 50 of the window part 31 is contiguously coplanar with the inner surface 51 of the flow tube portion 21 without a step or unevenness. The inner surface 50 of the window portion 31 and the inner surface 51 of the flow tube portion 21 are the surfaces defining the ventilation passage 41b of the sensor mounting portion 20, that is, the surfaces that contact the respiratory gas of the subject. In the illustrated embodiment, the inner surface 50 of the window portion 31 and the inner surface 51 of the flow tube portion 21 are formed in a planar shape. The inner surface 50 and the inner surface 51 may alternatively be formed as a non-step curved surface. A hydrophilic coating may be applied to the inner surface of the effective portion 32.

According to the gas measurement adapter 1 configured as described above, the inner surface 50 of the window portion 31 and the inner surface 51 of the flow tube portion 21 provided in the sensor mounting portion 20 are contiguously coplanar with each other without a stepped portion. Therefore, even when water droplets generated from the respiratory gas passing through the ventilation passage 41b of the sensor mounting portion 20 slide along the inner surface 51 of the flow tube portion 21, and the water droplets are prevented from remaining on the inner surface 50 of the window portion 31. Thus, the measurement light passing through the window portion 31 is prevented from being blocked by the water droplets, and the amount of the measurement light is suppressed from being reduced. Therefore, it is possible to suitably measure gas concentration of the respiratory gas of the subject by suppressing measurement errors resulting from the water droplets.

The ventilation passage 41b of the sensor mounting portion 20 is formed in the same shape as the bottom portion of the ventilation passage 41a of the first connection adapter 11 at the bottom portion of the ventilation passage 41b, and is formed in a narrow shape having a width defined by the inner surface 50 of the window portion 31 and the inner surface 51 of the flow tube portion 21 at the upper side of the bottom portion of ventilation passage 41b. Therefore, the water droplets generated in the ventilation passage 41b drop down to the bottom portion in the gravity direction along the non-step inner surface defined by the window portion 31 and the flow tube portion 21, and then slide toward one the ventilation passage 41a or the passage 41c direction without remaining at the window portion 31.

The window portion 31 includes the effective portion 32 and the outer peripheral portion 33 as described above, and the inner surface 50 of the window portion 31 is configured such that at least at the outer perimeter 34 of the effective portion 32 is contiguously coplanar with the outer peripheral portion 33 without a stepped portion. An inner surface of a portion of the outer peripheral portion 33 that is far from the outer perimeter 34 of the effective portion 32 may be configured non-coplanar with the inner surface 50 of the outer perimeter 34 of the effective portion 32 (may include a stepped portion). Specifically, for example, a groove (stepped portion) extending from the second connection adapter 12 side to the first connection adapter 11 side through the portion of the outer peripheral portion 33 that is far from the outer perimeter 34 may be formed to cause the water droplets generated from the respiration to flow. The inner surface 50 of the window portion 31 may have another configuration in so far as a stepped portion is not provided at a portion bordering the effective portion 32 (the portion adjacent to the effective portion 32). The flow tube portion 21 may be configured such that the inner surface 51 of the portion far from the window portion 31 is nonplanar with the inner surface 50 at the outer perimeter 34 of the effective portion 32 (may have a stepped portion).

According to the gas measurement adapter 1 configured as described above, even when water droplets are generated in the ventilation passage 41b of the sensor mounting portion 20, the water droplets are prevented from remaining between the outer perimeter 34 of the effective portion 32 and the outer peripheral portion 33. Accordingly, as described above, the measurement light passing through the window portion 31 is prevented from being blocked by the water droplets, and the amount of the measurement light is suppressed from being reduced. Therefore, it is possible to suitably measure the gas concentration of the respiratory gas of the subject by suppressing measurement errors resulting from the water droplets.

Figure 5:
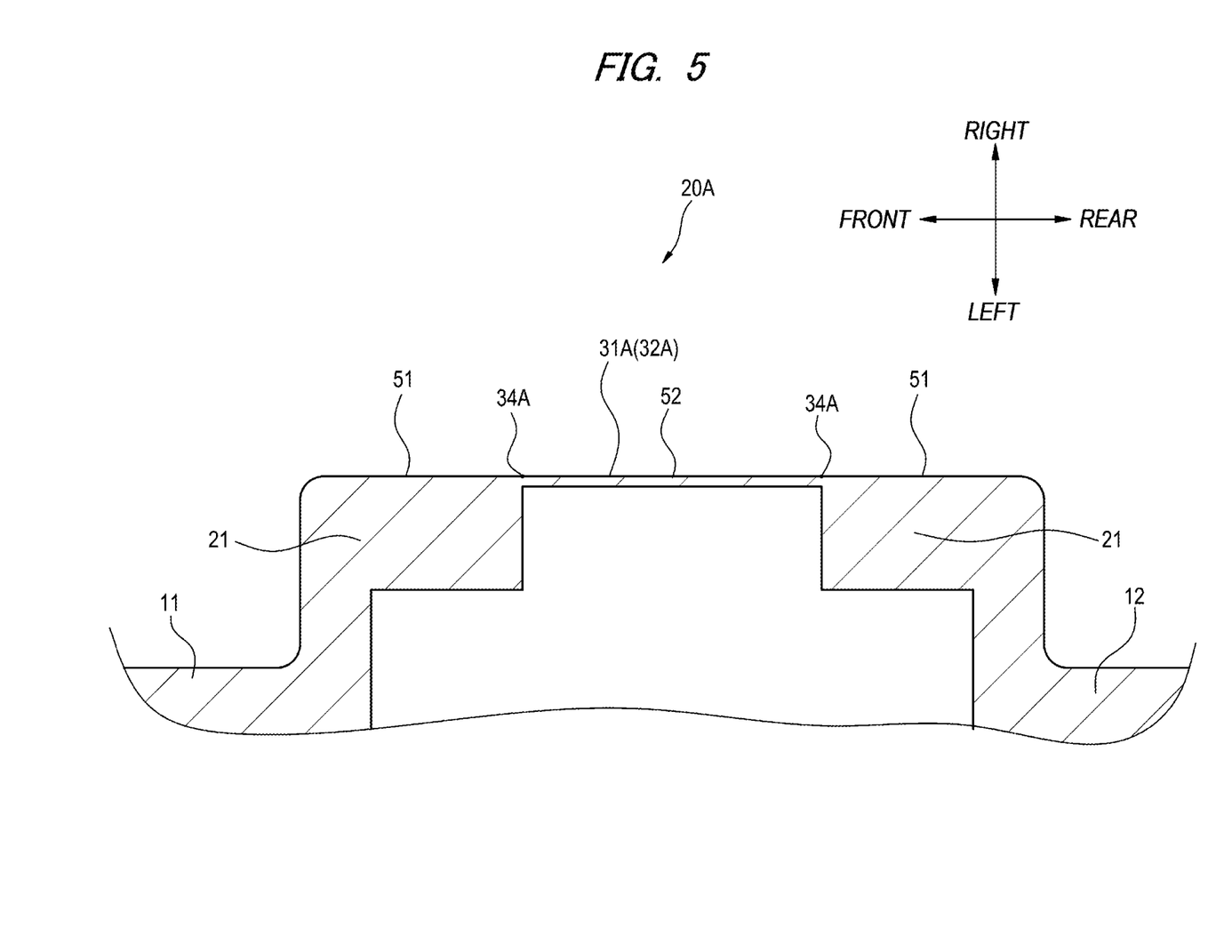
FIG. 5 is a cross-sectional view illustrating a modification of a window and a flow tube at the sensor mounting portion.

FIG. 5 illustrates a modification of the window portion and the flow tube portion of the sensor mounting portion, and is a cross-sectional view corresponding to the line of FIG. 1. The same elements as those of the foregoing embodiment are denoted by the same reference numerals, and description thereof will be omitted as appropriate.

The sensor mounting portion 20A illustrated in FIG. 5 is different from the window portion 31 of the sensor mounting portion 20 in that the entire window portion 31A is configured as the effective portion 32A and the outer peripheral portion is not provided. In the sensor mounting portion 20A, the inner surface 52 of the window portion 31A is configured such that the outer perimeter 34A of the window portion 31A is contiguously coplanar with the inner surface 51 of the flow tube portion 21 located at the outer periphery of the window portion 31A without a stepped portion. That is, the outer perimeter 34A of the window portion 31A on the inner surface of the window portion 31A is coplanar with the portion of the flow tube portion 21 bordering the outer perimeter 34A of the window portion 31A.

According to the sensor mounting portion 20A configured as described above, the inner surface 52 of the outer perimeter 34A of the window portion 31A and the inner surface 51 of the flow tube portion 21 on the outer periphery of the window portion 31A are contiguously coplanar with each other without a stepped portion. Therefore, even when water droplets are generated in the ventilation passage 41b (see FIG. 3) of the sensor mounting portion 20A, the water droplets can be prevented from remaining between the inner surface 52 of the outer perimeter 34A of the window portion 31A and the inner surface 51 of the flow tube portion 21. Thus, as described above, the measurement light passing through the window portion 31A is prevented from being blocked by the water droplets, and the amount of the measurement light is suppressed from being reduced. Therefore, it is possible to suitably measure the gas concentration of the respiratory gas of the subject by suppressing measurement errors resulting from the water droplets.

The presently disclosed subject matter is not limited to the embodiments described above, and various changes and modifications may be made therein. For example, the material, shape, size, numerical value, form, number, arrangement location, and the like of each element in the embodiments described above are optional and are not intended to limit the presently disclosed subject matter as long as the presently disclosed subject matter can be implemented.

What is claimed is:

1. A gas measurement adapter comprising:
   a flow tube portion configured to allow gas to pass through the flow tube portion; and
   a window portion configured to allow measurement light for measuring a component of the gas passing through the flow tube portion to pass through the window portion,
   wherein the window portion is thinner than the flow tube portion and is molded integrally with the flow tube portion,
   wherein the window portion comprises an effective portion configured to allow the measurement light to pass through the effective portion and an outer peripheral portion provided on an outer periphery of the effective portion,
   wherein an inner surface of the window portion is configured such that an outer perimeter of the effective portion is contiguously coplanar with the outer peripheral portion,
   wherein the inner surface of the window portion is contiguously coplanar with an inner surface of the flow tube portion, and
   wherein the inner surface of the window portion and the inner surface of the flow tube portion define a portion of a ventilation passage through which the gas passes inside the gas measurement adapter.

2. The gas measurement adapter according to claim 1, comprising a first connection adapter, a second connection adapter, and a sensor mounting portion provided between the first connection adapter and the second connection adapter, the sensor mounting portion comprising the flow tube portion and the window portion,
   wherein the flow tube portion is configured to allow respiratory gas flowing in from the second connection adapter to pass toward the first connection adapter.

3. The gas measurement adapter according to claim 2, wherein the ventilation passage is configured as a single passage extending through the first connection adapter, the sensor mounting portion and the second connection adapter.

4. The gas measurement adapter according to claim 3, wherein the ventilation passage in the sensor mounting portion is narrower in a light passing direction in which the measurement light passes through the gas measurement adapter via the window portion than in a direction perpendicular to the light passing direction and a gas flow direction in which the respiratory gas flowing in from the second connection adapter passes toward the first connection adapter.

5. The gas measurement adapter according to claim 1, wherein the inner surface of the window portion is configured such that the outer perimeter of the effective portion is contiguously coplanar with the outer peripheral portion without a stepped portion.

6. The gas measurement adapter according to claim 1, wherein the outer perimeter of the window portion on the inner surface of the window portion is contiguously coplanar with the portion of the flow tube portion bordering the outer perimeter of the window portion without a stepped portion.

7. The gas measurement adapter according to claim 1, wherein:
the portion of the ventilation passage defined by the inner surface of the window portion and the inner surface of the flow tube portion has a first width in a first direction and a second width in a second direction, the first width being narrower than the second width,
the first direction and second direction are perpendicular to each other and a gas flow direction of the gas passing through the flow tube portion.

8. The gas measurement adapter according to claim 7, wherein the first direction corresponds to a left-right direction and the second direction corresponds to an up-down direction.

9. The gas measurement adapter according to claim 8, wherein the second width in the second direction extends at least to a lower end of the window portion.

10. The gas measurement adapter according to claim 7, wherein the first direction corresponds to a light passing direction of the measurement light passing through the window portion.

11. A gas measurement adapter comprising:
a flow tube portion configured to allow gas to pass through the flow tube portion; and
a window portion configured to allow measurement light for measuring a component of the gas passing through the flow tube portion to pass through the window portion,
wherein the window portion is thinner than the flow tube portion and is molded integrally with the flow tube portion,
wherein an outer perimeter of the window portion on an inner surface of the window portion is contiguously coplanar with a portion of the flow tube portion bordering the outer perimeter of the window portion,
wherein the inner surface of the window portion is contiguously coplanar with an inner surface of the flow tube portion, and
wherein the inner surface of the window portion and the inner surface of the flow tube portion define a portion of a ventilation passage through which the gas passes inside the gas measurement adapter.

12. The gas measurement adapter according to claim 11, wherein:
the portion of the ventilation passage defined by the inner surface of the window portion and the inner surface of the flow tube portion has a first width in a first direction and a second width in a second direction, the first width being narrower than the second width,
the first direction and second direction are perpendicular to each other and a gas flow direction of the gas passing through the flow tube portion.

13. The gas measurement adapter according to claim 12, wherein the first direction corresponds to a left-right direction and the second direction corresponds to an up-down direction.

14. The gas measurement adapter according to claim 13, wherein the second width in the second direction extends at least to a lower end of the window portion.

15. The gas measurement adapter according to claim 12, wherein the first direction corresponds to a light passing direction of the measurement light passing through the window portion.

* * * * *

UNITED STATES PATENT AND TRADEMARK OFFICE
CERTIFICATE OF CORRECTION

PATENT NO. : 10,912,912 B2
APPLICATION NO. : 16/143608
DATED : February 9, 2021
INVENTOR(S) : Yuya Baba It is certified that error appears in the above-identified patent and that said Letters Patent is hereby corrected as shown below:

In the Specification

Column 2, Line 11, "along the line of" should read -- along the line III-III of --

Column 3, Line 34, "along the line of" should read -- along the line III-III of --

Column 5, Line 45, "corresponding to the line of" should read -- corresponding to the line III-III of --

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*